United States Patent
Popa et al.

(10) Patent No.: US 10,588,331 B2
(45) Date of Patent: Mar. 17, 2020

(54) METHOD FOR CONVERTING FOOD WASTE AND OTHER BIOLOGICAL WASTE INTO INVERTEBRATE FEED

(71) Applicant: River Road Research, Inc., Tonawanda, NY (US)

(72) Inventors: Radu Popa, Reseda, CA (US); Kenneth H. Nealson, South Pasadena, CA (US); Matthew Schechter, Long Beach, CA (US)

(73) Assignee: River Road Research, Inc., Tonawanda, NY (US)

( * ) Notice: Subject to any disclaimer, the term of this patent is extended or adjusted under 35 U.S.C. 154(b) by 319 days.

(21) Appl. No.: 15/528,983

(22) PCT Filed: Jul. 29, 2015

(86) PCT No.: PCT/US2015/042646
§ 371 (c)(1),
(2) Date: May 23, 2017

(87) PCT Pub. No.: WO2016/085545
PCT Pub. Date: Jun. 2, 2016

(65) Prior Publication Data
US 2017/0265496 A1    Sep. 21, 2017

Related U.S. Application Data

(60) Provisional application No. 62/084,959, filed on Nov. 26, 2014.

(51) Int. Cl.
| | |
|---|---|
| *A23K 10/12* | (2016.01) |
| *A23K 50/90* | (2016.01) |
| *B09B 3/00* | (2006.01) |
| *B09B 5/00* | (2006.01) |
| *A23K 10/00* | (2016.01) |
| *C12M 1/00* | (2006.01) |

(52) U.S. Cl.
CPC .............. *A23K 10/12* (2016.05); *A23K 50/90* (2016.05); *B09B 3/00* (2013.01); *B09B 5/00* (2013.01);
(Continued)

(58) Field of Classification Search
CPC ........ A23K 10/12; A23K 50/90; A23K 10/00; B09B 3/00; B09B 5/00; C12M 21/00; Y02W 30/78
See application file for complete search history.

(56) References Cited

U.S. PATENT DOCUMENTS

| | | | | |
|---|---|---|---|---|
| 5,312,632 | A | * | 5/1994 | Simsa ..................... C05F 17/00 426/53 |
| 5,411,727 | A | | 5/1995 | Mullins et al. |

(Continued)

FOREIGN PATENT DOCUMENTS

| | | | | |
|---|---|---|---|---|
| CN | 103504151 B | | 6/2015 | |
| DE | 3841928 A1 | * | 6/1990 | ........... A23N 17/002 |

(Continued)

OTHER PUBLICATIONS

Machne translation of DE3841928 patent published 1990 (Year: 1990).*

(Continued)

*Primary Examiner* — C. Sayala
(74) *Attorney, Agent, or Firm* — Harris Beach PLLC; Laura W. Smalley

(57) ABSTRACT

Biological waste such as food, organic or other biologically-derived waste is converted into shelf-stable and health-safe invertebrate feed. The method for converting includes pre-treating waste by fragmenting, reducing microbial contaminants, optionally amending with components that optimize fermentation, inoculating with microorganisms and mixing. Fermentation takes place in a bioreactor and produces (Continued)

Figure 1:
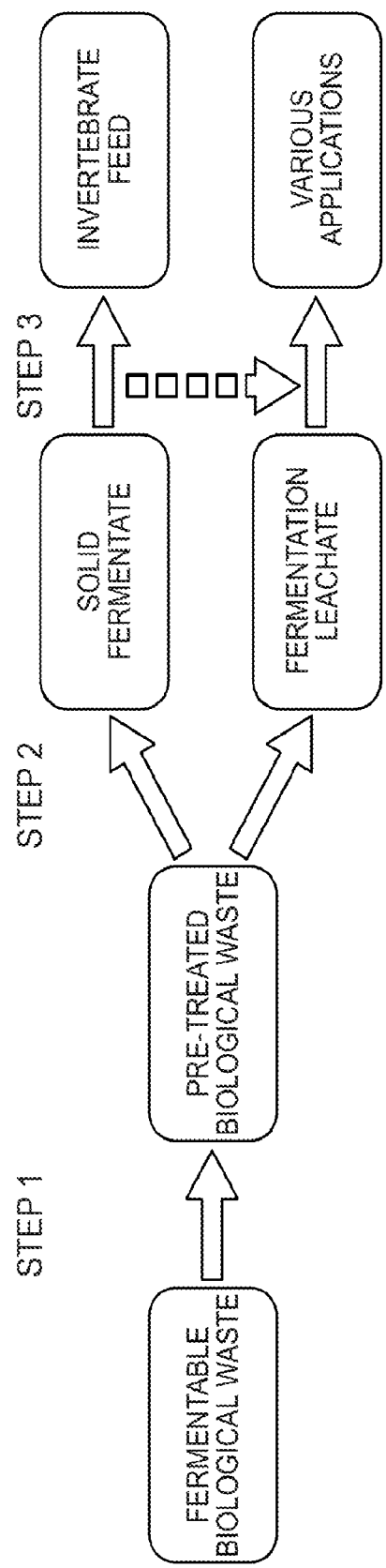

fermentation leachate and solid fermentate. In the post-treatment steps, the solid fermentate is separated from the fermentation leachate. The solid fermentate is ground, dewatered and milled. The solid fermentate can be used as an invertebrate feed with or without further processing.

21 Claims, 2 Drawing Sheets

(52) U.S. Cl.
CPC ........... *A23K 10/00* (2016.05); *B09B 2220/00* (2013.01); *C12M 21/00* (2013.01); *Y02W 30/78* (2015.05)

(56) References Cited

U.S. PATENT DOCUMENTS

| | | |
|---|---|---|
| 8,481,295 B2 | 7/2013 | van Leeuwen et al. |
| 8,815,539 B1 | 8/2014 | Popa et al. |
| 2009/0004714 A1 | 1/2009 | Norholm et al. |
| 2010/0183756 A1 | 7/2010 | Kobayashi et al. |
| 2012/0187228 A1 | 7/2012 | Camp et al. |

FOREIGN PATENT DOCUMENTS

| | | | | |
|---|---|---|---|---|
| GB | 2167639 A | * | 6/1986 | ............. A23K 10/26 |
| WO | WO-2009/067771 A1 | | 6/2009 | |
| WO | WO-2009/111066 A1 | | 9/2009 | |

OTHER PUBLICATIONS

IPOS/SG, Search Report and Written Opinion for corresponding Singapore Application No. 1120170420X, dated Jun. 21, 2018. (7 pages).

PCT Third Party Observation filed in corresponding International Application No. PCT/US2015/042646, dated Sep. 26, 2016.

ISA/US, International Search Report and Written Opinion for corresponding International Application No. PCT/US2015/042646, dated Oct. 26, 2015. (13 pages).

\* cited by examiner

METHOD FOR CONVERTING FOOD WASTE AND OTHER BIOLOGICAL WASTE INTO INVERTEBRATE FEED

CROSS-REFERENCE TO RELATED APPLICATIONS

This application is a national stage application under 35 U.S.C. § 371 of PCT Application No. PCT/US2015/042646, filed Jul. 29, 2015, which claims priority to and the benefit of U.S. provisional patent application Ser. No. 62/084,959, entitled Method for Converting Food Waste and Other Biological Waste into Invertebrate Feed, filed Nov. 26, 2014, which is incorporated herein by reference in its entirety.

1. TECHNICAL FIELD

The present invention relates to methods for converting biological waste, organic waste, food waste and other biologically-derived waste materials into invertebrate feed.

2. BACKGROUND OF THE INVENTION

The world's needs for animal-derived protein products (such as fish meal, soymeal and peanut meal) in animal feed and aquaculture applications are growing rapidly. The needs for fish meal are outstripping the ocean's ability to regenerate the forage fish that are harvested to manufacture fish meal. Precipitous and unsustainable decline in ocean fish stocks put strain on aquaculture and poultry culture. Vegetal sources of proteins, such as soy meal and peanut meal, are also in limited supply because they are costly to produce and also because they are usable as human food. Growing vegetal biomass (such as soy and peanuts) for the purpose of feeding livestock is not sustainable when these materials can be used to feed humans directly.

Insect-based biomass can be utilized in animal feeds as a substitute for animal-derived proteins (such as the proteins in fish meal) or plant-derived proteins (such as the proteins in soy meal or peanut meal). One possible approach for insect rearing is to utilize pre- and post-consumer food waste and other biological wastes as feedstock. Cultured invertebrates, such as earthworms, meal worms, shrimps, prawns or crayfish, crickets and fly larvae, that can be used to feed humans or animals, or to make fertilizers, can be fed with food waste and other biological wastes or derivatives of food waste and other biological wastes.

According to the United Stated Environmental Protection Agency, using food waste and other biological wastes to feed invertebrates is classified as an industrial use and is preferable to composting or landfilling (http://www.epa.gov/foodrecovery/, last visited Jul. 2, 2015). However, the collection, transportation and storage of unprocessed food waste before it is fed to invertebrates can lead to many problems. These problems include fast rates of putrefaction of the food waste, the release of decaying liquids and odors, the propagation or multiplication of food-borne pathogens, the production of food-borne toxins hazardous to humans and livestock, the production of toxins that are toxic for microorganisms and the attraction of vermin.

If there is an asymmetry between supply and demand, excess food waste becomes a health hazard and must be landfilled, composted or burned, all of which are inferior as uses to the industrial generation of animal feed products. Hence, decaying biological waste (which, as used herein, is organic waste, food waste, or other biologically-derived waste) must be collected and processed efficiently as it is generated.

Feeding urban food waste (whether raw or processed) directly to livestock increases the risk of spreading food-borne pathogens and is not efficient in industrial animal farms. Food waste, especially post-consumer urban and domestic food waste, typically contains materials that are un-digestible or hazardous to animals (including plastic, paper, cutlery, spices, wax, etc.). Using food waste as fertilizer (whether raw or processed) only works in limited cases. Many types of food waste and food waste derivatives are rich in food preservatives (such as sodium and chloride) that are undesirable for plant growth. Raw or insufficiently mineralized food waste increases the risk of spreading microbial pathogens and of molding in soil with release of poisonous chemicals such as aflatoxins.

Citation or identification of any reference in Section 2, or in any other section of this application, shall not be considered an admission that such reference is available as prior art to the present invention.

3. SUMMARY OF THE INVENTION

A method is provided for processing decayable biological or organic waste before it turns hazardous, and converting it into stable feedstock for raising or growing invertebrates.

In one embodiment, a method for converting biological waste to invertebrate feed is provided, the method comprising:
  pre-treating biological waste, wherein the pretreating comprises:
    fragmenting the waste,
    reducing microbial contaminants in the waste,
    inoculating the waste with microorganisms, and
    mixing the waste;
  providing a bioreactor;
  performing fermentation of the waste under anaerobic conditions, wherein performing fermentation comprises fermenting the waste in the bioreactor to produce a fermentation product comprising fermentation leachate and solid fermentate;
  post-treating the fermentation product, wherein the post-treating comprises:
    separating solid fermentate from fermentation leachate in the fermentation product,
    grinding the solid fermentate,
    dewatering the solid fermentate, and/or
    milling the solid fermentate,
thereby producing an invertebrate feed.

In an embodiment, the biological waste is optimal biological waste or low efficiency biological waste.

In another embodiment, the pre-treating comprises amending the waste with fermentation-optimizing agents.

In another embodiment, the method comprises monitoring the fragmenting continuously and/or controlling the fragmenting to optimize the average particle size and particle size variance.

In another embodiment, the method comprises monitoring the fermenting.

In another embodiment, the method comprises analyzing the fermentation leachate.

In another embodiment, the method comprises controlling the temperature of fermentation.

In another embodiment, the method comprises controlling the pH of fermentation.

In another embodiment, the method comprises adding lactic acid to the fermentation.

In another embodiment, the method comprises controlling the Brix % of fermentation In another embodiment, the density of microorganisms inoculating the waste is $\geq 10^5$-$10^6$ cells per ml.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated, enlarged, exploded, or incomplete to facilitate the understanding of the invention.

FIG. 1. Flow chart of one embodiment of the method for converting food waste and other biological wastes to invertebrate feed. The main steps of this method are: (1) pre-treating, (2) performing fermentation, and (3) post-treating the fermentation product to produce two end products: fermentation leachate and invertebrate feed.

Figure 2:
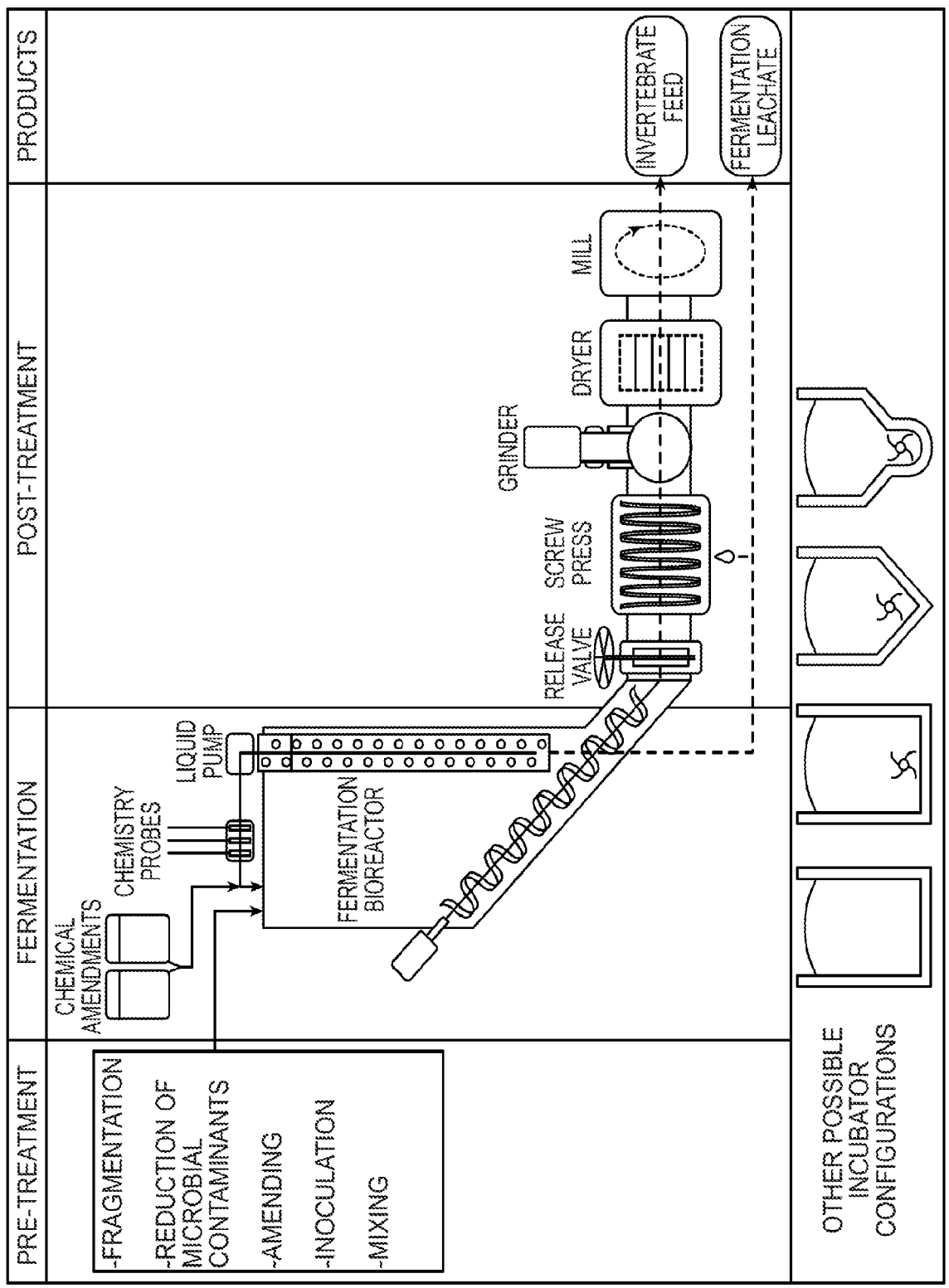

FIG. 2. Diagram of an example of a facility that can be used to carry out the disclosed method. The diagram shows an embodiment of the method being carried out in the facility. Fermentable biological, organic, food or other biologically-derived waste is fragmented, treated to reduce microbial contaminants, optionally amended with components or agents for optimizing fermentation, inoculated with microorganisms and mixed. Fermentation occurs in a bioreactor, and during fermentation, the leachate is circulated as needed using, e.g., a liquid pump and monitored for pH, ammonium, temperature and salinity using chemistry probes. The probes are used to monitor the evolution of the fermentation and help make decisions about duration of fermentation and other amendments to make for improving fermentation. The tube with the screw beneath the fermenter is an auger used to pull fermented solids out of the system. The leachate can, if necessary, be amended to control the progression of the fermentation. Two materials are produced: fermentation leachate and solid (or "wet") fermentate. The fermentation leachate is removed for other uses. The solid fermentate can be fed to invertebrates directly or dewatered (e.g., using a screw press), ground (e.g., using a grinder, dewatered or dried (e.g., in a dryer) and milled (e.g., in a mill) to produce shelf-stable invertebrate feed used to feed invertebrates. The bottom half of the diagram shows examples of other possible incubator configurations shown as cross-sections. The 4-armed profiles depicted at the bottom of some of the incubator configurations represent cross-sections through auger devices used to remove materials at the bottom of the fermenter.

5. DETAILED DESCRIPTION OF THE INVENTION

Methods are provided for converting biological waste, including food waste, organic waste and other types of biologically-derived waste, into shelf-stable and health-safe invertebrate feed. In one embodiment, the method comprises: pre-treating waste by fragmenting, reducing microbial contaminants, inoculating with microorganisms and mixing. In another embodiment, pre-treating waste comprises amending the waste with components or agents that optimize fermentation ("fermentation-optimizing agents"). Fermentation takes place in a bioreactor and produces a fermentation product comprising or consisting of two components: fermentation leachate and solid fermentate.

After fermentation, the solid fermentate is separated from the fermentation leachate. The solid fermentate is ground, dewatered and milled. The solid fermentate can be used as invertebrate feed with or without further processing.

As used herein, biological waste includes organic waste, food waste or other biologically-derived waste.

As used herein, "organic" waste is waste that comprises organic compounds. An organic compound is any member of the large class of gaseous, liquid, or solid chemical compounds whose molecules contain carbon. Examples of organic molecules include but are not limited to: hydrocarbons, phenolic compounds, proteins, fats, sugars, nucleic acids, vitamins, and amines containing carbon atoms. For historical reasons, a few types of carbon-containing compounds, such as carbides, carbonates, simple oxides of carbon (such as CO and $CO_2$), and cyanides are considered inorganic.

As used herein, "organic" is not employed as the commercial term "organic," which is used to certify food that has been produced in a natural way, clean of chemical fertilizers, pesticides, hormones and chemical food stabilizers.

In one embodiment, the method for converting biological waste to invertebrate feed comprises:
  pre-treating biological waste, wherein the pretreating comprises:
    fragmenting the waste,
    reducing microbial contaminants in the waste,
    inoculating the waste with microorganisms, and
    mixing the waste;
  providing a bioreactor;
  performing fermentation of the waste under anaerobic conditions, wherein performing fermentation comprises fermenting the waste in the bioreactor to produce a fermentation product comprising fermentation leachate and solid fermentate;
  post-treating the fermentation product, wherein the post-treating comprises:
    separating solid fermentate from fermentation leachate in the fermentation product,
    grinding the solid fermentate,
    dewatering the solid fermentate, and/or
    milling the solid fermentate,
thereby producing an invertebrate feed.

For clarity of disclosure, and not by way of limitation, the detailed description of the invention is divided into the subsections set forth below.

5.1. Classes of Biological Wastes

Optimal Biological Waste

Optimal biological waste is fresh biological waste and does not include rotten food, and does not contain unsafe levels of food-borne pathogens, food-borne toxins and chemical contaminants. Optimal biological waste materials are rich in small sugars, starch, and small particle cellulose, and low in nitrogen and fat. These materials are safe to use in any proportion as main fermentation ingredients and produce high yield and high quality invertebrate feed. Examples of such materials include, but are not limited to: pre- and post-consumer food waste (the present method is tolerant of high salt and/or preservatives concentration); and fermentable food waste from animal, dairy and vegetal oil waste. Optimal biological waste can be, for example, vegetables and fruit, such as grocery waste, cantinas and restaurant food waste, expired food, commercial "food court" food waste, farmers' market food waste, bakery waste and cooked food waste); algal biomass; microbial mat biomass;

oil-containing vegetal materials (such as fruit and seeds leftover after oil extraction); sugar-containing vegetal materials (such as leftovers from the sugar industry such as sugar cane, sugar beets, molasses, corn syrup, honey, and fruit juice industry leftovers); starch-containing vegetal materials (such as vegetal and fruit peels and seeds, bran, seed leftovers and distillation refuse); non-woody vegetal biomass from agriculture, gardening and landscaping (such as trimmed grass, leaves, stems, roots, rhizomes, chaff, spoiled silage, and undesirable and/or invasive leafy vines and weeds such as Kudzu and Dame's rocket); non-woody wetland biomass (including but not limited to invasive and/or undesirable species such as water hyacinth, water lettuce, duckweed, algae, cattail and papyrus); residues of fermentation (such as byproducts of industries producing beer, wine, cider, vinegar and distillates); and sugar-rich hydrolysates (such as byproducts of the cellulosic ethanol industry and hydrolysates of various vegetal materials).

In an embodiment, proteins and fats (together) do not constitute more than approximately 30% of optimal biological waste.

Low Efficiency, Safe Biological Waste

Low efficiency biological waste that can be used can be either "safe" or "unsafe." Low efficiency, "safe" biological waste suitable for use in the methods disclosed herein includes materials that have low efficiency in being fermented and low efficiency in producing invertebrate feed, yet are safe to use and can be mixed in any proportion with optimal biological waste (as described above) during or after fermentation. Low efficiency, safe biological waste materials can be used as a source of fiber, nutrients, bulking agents, to modify permeability (and thus leachate draining rates in bioreactors), as a source of carbon and carbohydrates and to control the water content in fermentation mixtures. These materials comprise primarily cellulose, hemicellulose and lignin, and include woody biomass, hay, straw, corn stover, corn cobs, woody water plants or wetland plants (such as reeds, bamboo and sugar cane), fabric and fibers of biological origin (e.g., cotton, linen, jute and hemp) and paper and cardboard products (that do not contain plastic amendments, chemical dyes, non-biological glue and heavy metals). These materials may also include spent low quality materials resulting from other forms of industrial fermentations such as composting and anaerobic digestion. These materials are partly hydrolyzed with the help of cellulolytic enzymes and therefore are more efficiently processed if they are fragmented, hydrolyzed before they are introduced in bioreactors, or fermented longer (commonly more than two weeks) in bioreactors.

Low Efficiency, Unsafe Biological Waste

Low efficiency, "unsafe" biological waste includes materials that are rich in organic nitrogen of animal origin and/or fat, that decay rapidly and/or have low efficiency of being fermented and that are difficult to stabilize, i.e., they turn moldy, rot or turn rancid prior, during or after fermentation. These materials can be present in bioreactors and can be stabilized if the fermentation proceeds correctly, but can only be added in controlled proportions, as described below. These materials can add nutrients (e.g., saturated fats, sterols, organic nitrogen, phosphorus, and aromatic amino acids) that are valuable in invertebrate feeds, but they also pose significant health risks (owing to growth of food-borne pathogens and food-borne toxins). When added in too large a proportion, low efficiency, unsafe biological wastes can negatively influence the fermentation process by chemical inhibition, by limiting water circulation, by limiting wetting and dissolution or by alkalization.

Examples of such low efficiency, unsafe biological waste materials include but are not limited to: animal parts (meat, fat, entrails, fish cleaning byproducts, skin, scales, cartilages and bones and animal gut content); animal-rich food waste; liquids rich in animal components (such as blood, plasma, animal-derived food concentrates and washouts with animal materials); dairy and dairy contaminated products; animal fat; and vegetal oil. A low proportion of such materials in food waste to be processed by the methods disclosed herein is acceptable, as long as the material(s) are well mixed with the fermentation mixture, are not contaminated with microbial pathogens, are not decomposed, do not contain hazardous levels of toxic chemicals (including but not limited to hydrogen sulfide, amines, heavy metals, aflatoxins, antibiotics, detergents, metabolic inhibitors, pesticides or heavy metals), do not interfere with the evolution (either chemistry or duration) of the fermentation process after the target chemistry and pH for the fermentation process have been reached, do not increase the abundance of microbial pathogens during fermentation, do not interfere with the reduction of microbial pathogens during fermentation, and do not increase the concentration of food-borne toxins during or after fermentation.

The amount of low efficiency unsafe biological waste that can be tolerated in the method is positively correlated with the concentrations of microbial metabolites produced by the complex microbial inoculum converting water-soluble carbohydrates that are present in the food waste or added by way of amendment with molasses or other sugars.

The combination of various metabolites that can be used to produce a stabilizing effect on proteins, nucleic acids and fats contained in low efficiency unsafe biological waste are known in the art. Many examples of how various combinations of metabolites (e.g., lactate, formate, acetate, propionate, butyrate, pH, alcohols and esters) and lack of oxygen stabilize proteins and prevent putrefaction, ammonification and alkalization are found in the references listed herein (see for example: Mercier et al., 1992; Weinberg et al., 2003; Cai, 1993; Middleton and Ferket, 2001).

Undesirable Biological Waste

Undesirable biological waste that should be avoided in carrying out the methods disclosed herein includes materials that are of biological origin and in some cases, rich in energy and/or nutrients, but pose significant health risks and are generally not allowed to enter the industrial food chain. Such materials include, but are not limited to: manure, sewage materials, toxin-producing cyanobacterial or algal biomass (toxins that are dangerous to humans, livestock and pets), animals and plants killed owing to algal blooms, animal bedding, medical and veterinary waste, hygiene products, and natural antibiotics and growth inhibitors. These materials are (or can become) toxic, and are contaminated with microbial pathogens or represent a medium for the growth, maintenance or spreading of microbial pathogens. Some of these materials, such as algal bloom biomass and animals killed during algal blooms, often contain high levels of toxins of biological origin produced by microorganisms such as cyanobacteria and molds.

Undesirable Non-biological Waste

Undesirable non-biological waste that should be avoided in carrying out the methods disclosed herein includes materials that can be present in some waste streams at levels that are hazardous to the health of animals and people. These materials may be inorganic or organic in composition but of non-biological origin. Such materials should not be included in the fermentation mixture because they are non-fermentable, non-digestible, toxic or may release toxic byproducts.

Examples of undesirable non-biological waste materials include, but are not limited to: toxic inorganic chemicals (e.g., products of chemical industry and mining activity byproducts such as heavy metals, cyanide, arsenate, ammonia, nitrite, mine tailing materials, even those that are rich in microorganisms; residues of microbial mining; and leachates of wood hydrolysis), oil/coal and oil/coal derivatives, detergents, pesticides, plastics (whether biodegradable or not), and hazardous organic chemicals of non-biological origin (such as solvents, paints, drugs, acrylamide, dioxin, hormones, synthetic antibiotics and other types of metabolic inhibitors of abiotic origin or antibiotics).

5.2. Method for Converting Biological Waste into Invertebrate Feed

Methods for converting biological waste (food, organic or biologically-derived waste) into invertebrate feed are described below.

An overview of one embodiment of a method for converting biological waste into invertebrate feed is shown in the flow chart in FIG. 1. Fermentable food waste is pre-treated for fermentation. Fermentation is carried out in a bioreactor, yielding solid fermentate and fermentation leachate. Solid fermentate is converted to invertebrate feed and, in certain embodiments, can be used to produce more fermentation leachate. The invertebrate feed (which can be produced with various levels of processing and water content) can be used as a feed directly or used as a component in feeds for various invertebrates including but not limited to insects, worms, crustaceans and mollusks. Depending on the target invertebrate to be fed, various proportions of other materials known in the art (such as proteins, fats, leachate, carbohydrates, vitamins, minerals, metal chelators, enzyme inhibitors and antioxidants) can be included in various feed formulas. Some invertebrates such as black soldier fly (*Hermetia illucens*) larvae can be fed with invertebrate feed exclusively. The fermentation leachate can be used for other applications such as producing chemicals such as melanin (see PCT application no. PCT/US2014/41118 (WO2014/197708A1) by Popa et al., filed Jun. 5, 2014 and published Dec. 11, 2014; U.S. Pat. No. 8,815,539 to Popa et al., Aug. 26, 2014), fertilizers and as part of feed formulations.

FIG. 2 is a diagram of an example of a facility that can be used to carry out the method and shows an embodiment of the method being carried out in the facility. Fermentable biological, organic, food or other biologically-derived waste is fragmented, treated to reduce microbial contaminants, optionally amended with components or agents for optimizing fermentation, inoculated with microorganisms and mixed. Fermentation occurs in a bioreactor, and during fermentation, the leachate is circulated as needed using, e.g., a liquid pump and monitored for pH, ammonium, temperature and salinity using chemistry probes. The probes are used to monitor the evolution of the fermentation and help make decisions about duration of fermentation and other amendments to make for improving fermentation. In FIG. 2, the tube with the screw beneath the fermenter is an auger used to pull fermented solids out of the system.

The leachate can, if necessary, be amended to control progression of the fermentation. The materials that are produced are fermentation leachate and solid (or "wet") fermentate. The fermentation leachate is removed for other uses. The solid fermentate can be fed to invertebrates directly or dewatered (e.g., using a screw press), ground (e.g., using a grinder, dewatered or dried (e.g., in a dryer) and milled (e.g., in a mill) to produce shelf-stable invertebrate feed used to feed invertebrates.

The bottom half of the diagram in FIG. 2 shows examples of other possible incubator configurations shown as cross-sections. The 4-armed profiles depicted at the bottom of some of the configurations represent cross-sections through auger devices used to remove materials at the bottom of the fermenter.

In an embodiment, pre-treating waste (FIG. 2) can comprise fragmenting, reducing microbial contaminants, optionally amending with components or agents for optimizing fermentation, inoculating with microorganisms and/or mixing. Components or agents for optimizing fermentation ("fermentation-optimizing agents") include, but are not limited to bran, sugars, water, lignocellulose and minerals.

Fragmenting waste (FIG. 2) can be used to produce particles that are suitable for use in fermentation and post-treatment, e.g., in terms of size, size homogeneity and permeability of the particles. Details about fragmenting waste and about suitable particles are given in Section 5.2.1.

Reducing microbial contaminants (FIG. 2) has the purpose of reducing or eliminating undesirable microorganisms or microorganisms that, given favorable conditions may, for example, over-compete fermenting microorganisms added to bioreactors, divert the fermentation process from its desired direction, pose a health risk during pre-treatment, or result in health risks that cannot be resolved by fermentation and post-treatment. Details about reducing microbial contaminants are given in Section 5.2.2.

Amending (FIG. 2) is optional and can be conducted in certain embodiments to produce mixtures suitable or optimized for fermentation. Amending can make the mixture predictable for purposes of fermentation. Amending depends on the properties of the input materials. Some materials such as fruit pulp mixed with vegetables and beer mash do not need amending because they have sufficient chemicals needed for fermentation.

For example, the skilled artisan can determine the approximate composition of the source materials and determine whether they contain sufficient fermentable sugars to produce a leachate with Brix % of approximately of 6-10. The nitrogen content should be sufficiently low to not produce ammonification and alkalization during fermentation. The skilled artisan will identify materials that compact during fermentation and restrict leachate circulation; they will add more fiber material to the mixtures to help the circulation of the leachate.

Most common amendments are bran, sugars, water, lignocellulose and minerals. Although addition of salts can also be used to stabilize biological waste, and some invertebrates are able to eat food with increased salt content or to live in media with increased salt content, the addition of salts limits the subsequent use of leachate in various applications, for example, making fertilizers. The reasons for adding various amendments, and target compositions for fermentation mixtures, are discussed in Section 5.2.3.

Inoculating with microorganisms (FIG. 2) is done with mixed cultures of bacteria and yeasts selected for the capacity to grow in anaerobic, acidic and mesophilic conditions. These microbes are also selected to hydrolyze starch and cellulose, to heteroferment sugars to alcohols and organic acids, and/or to degrade oxalate, and/to degrade polyphenols, to inhibit the growth of other microorganisms predominantly by producing a wide diversity of secondary metabolites, and low yield of soluble alkali (such as ammonia and organic amines). Mixed cultures for inoculation can contain microbes that are non-pathogenic and will not produce toxins to animals, fungi or other bacteria. Details about the species of microorganisms used in inocula, physiology, sources of microorganisms, density at inoculation and examples of undesirable toxins are given in Section 5.2.4.

Mixing conducted prior to fermentation (FIG. 2) has the purpose of homogenizing the fermenting materials and facilitating evaluation of the quality of the fermentation mixture. Details about mixing are given in Section 5.2.5.

Fermenting (FIG. 2) can take place in a monitored and controlled reaction space, also referred to herein as a bioreactor. Details about the types of fermentation that can be used in the method, types of fermentation bioreactors that can be used, conditions applied during fermentation, fermentation indicators, and means of monitoring and controlling the fermentation process, fermentation rate and about end point fermentation parameters are given in Section 5.3.

Post-treatment (FIG. 2), the fermentation product is collected and the solid fermentate is separated from the fermentation leachate. The solid fermentate is ground, dewatered and milled. Details about post-treating the fermentation product are given in Section 5.4.

The method generates fermentation leachate and solid fermentate, which are described in Section 5.4. The fermentation leachate has many applications including producing melanin, feed amendments and fertilizers. The solid fermentate (the wet solid fraction of the fermented material) is ground, dried and milled to yield a stable invertebrate feed. In some cases (such as in the cultivation of Black Soldier Fly larvae (BSFL)), the invertebrate feed can also be used as is, without conducting any post-treatment step(s) as discussed above.

5.2. Pre-treating Biological Waste

This section describes various pre-treating steps in the method that can be conducted, singly, sequentially or in combination, on biological waste to carry out the production of invertebrate feed from biological waste.

5.2.1. Fragmenting

Fragmenting (or fragmentation) is used to produce particles that are suitable or optimal (in terms of size and size homogeneity) for fermentation and/or post-treatment. Fragmentation can also be used to control the flow rate of leachates and liquids. Very fine particles increase fermentation rate and release of water from cells, but also increase the hydrophilic surface area, make drainage of the leachate more difficult, lead to loss of material in the form of fine suspensions in leachate and increase the cost of dewatering. Very large particles make it difficult to mix the material, produce heterogeneous mixtures with hard to predict evolution of fermentation, difficult to transfer through pipes, slow down the fermentation process, have negative effects on the stabilization of waste, lower the capability to eliminate pathogens, increase the risk of food-borne toxins, inhibit the release of water from cells during fermentation and increase the cost of dewatering. Highly heterogeneous mixtures slow down fermentation, make fermentation uneven inside bioreactors, can clog fermenting mixtures by producing blockages in draining the leachate, limit the capacity to control the fermentation process and increase the risk of alkalization, food-borne pathogens and food-borne toxins.

In one embodiment, the particles in a fermenting mixture can be in the 1 mm to 50 mm size range, with an average of approximately 20-30 mm. Size and shape of particle fragmentation pre-treatment can vary dramatically, however, depending on the fermentation feedstock and optimizing the fermentation to various circumstances.

In one embodiment, the level of fragmentation is monitored continuously and controlled to optimize the average particle size and particle size variance. This can vary from case to case and for various types of food waste depending on how fast fermentation occurs and how easily the leachate drains. The capacity to drain the leachate, to monitor its chemistry and to intervene during fermentation makes the method predictable and decreases health risks and system crashes owing to fermentation going awry. With regard to waste particle size, the following guidelines can be used:

if the fermentation rate is too fast, then the particles may be too small;

if the fermentation rate is too slow, then particles may be too large;

if the total amount of leachate produced is too little, then particles may be too large;

if the total amount of leachate produced is too large, then particles may be too small;

if the leachate drainage rate is very low, then particles are too small or the mixture may be too heterogeneous and small particles clog the spaces between large particles.

To sum up these general parameters, the permeability of the biological waste to be converted should be at such a level that the biological waste to be converted can be completely re-inoculated with an amended leachate faster than the doubling time or change in composition owing to the metabolism of microorganisms. Recommended values for the fermentation rate, the amount of leachate produced and the rate of leachate drainage are discussed in the "Fermentation" Section 5.3.

5.2.2. Reducing Microbial Contaminants

Reducing microbial contaminants has the purpose of lowering the number or eliminating undesirable microorganisms, such as microorganisms that over-compete with fermenting microorganism in bioreactors, divert the fermentation process from its target direction, or poses a health risk during pre-treatment or result in health risks that cannot be resolved by fermentation and post-treatment.

Methods for lowering or eliminating undesirable microorganism include, but are not limited to heating, steaming, radiation, autoclaving, and oxidation.

In one embodiment of the method, lowering or eliminating undesirable microorganisms is not necessary. This choice is made when no such microorganisms are present or because of their low density they do not pose a risk.

In another embodiment of the method, biological waste is treated for lowering or for eliminating microorganisms before it is fermented. Such treating depends on the state of decay and contamination of the waste with pathogenic or potentially harmful microorganisms, or microorganisms known to produce toxins or with microorganisms not useful in fermentation that are in higher abundance than the inoculated microorganisms (approximately $10^5$ cells per ml). As a general guideline, if the waste material shows evidence of fermentation, smells of decay or rot or is moldy, then contamination with undesirable microorganisms can be assumed. Sterilization of the incoming feedstock, through methods such but are not limited to gamma radiation, is an option when pathogenic contamination is assumed. If the opposite is true, then adding inoculum at a level of $10^5$ cells per ml will in most cases solve the problem, provided that the composition of the source material and the fermentation conditions are controlled within specifications (discussed below).

5.2.3. Amending

Amending is an optional process that can be conducted during pretreatment and has the purpose of producing mixtures that are suitable (e.g., optimized) for fermentation. Any suitable amendment known in the art can be used. Amendments such as bran, sugars, water, lignocellulose and minerals can be used. Bran is added as a source of starch, carbon, phosphorus, fine-particle cellulose fibers and spores of cellulolytic strains of *Clostridium* spp. Bran from various sources can be used including rice, corn, wheat, oats, barley and millet. The amount of bran in fermentation mixtures is approximately 5-10% of the dry weight of the biological waste. In one embodiment of the method more than 10% bran can be used. Adding excessive amount of bran makes fermentation faster, and may result in more acidic pH sooner, and higher concentration of metabolic inhibitors in the final product. Yet, if stabilization can be obtained with less bran, then the use of less bran may be recommended, because the cost of bran is, in most cases, larger than the cost of fermentable biological waste. The abundance and availability of bran that is more suitable for particular local conditions, costs, source materials and fermentation conditions can be monitored and adjusted for desired parameters.

Sugars (mixtures of mono- and disaccharides) are added when the concentration of sugars and starch from the source materials is too low, or the ratio between fermentable nitrogen (proteins, amino acids and nitrogenous bases) and fermentable carbohydrates (sugars and starch) is too high, inhibiting the acid fermentation process. An optimal or suitable C:N ratio for achieving a healthy fermentation is 25:1 to 45:1 (Kim et al. 2006; Tembhurkar and Mhaisalkar, 2007; Manikandan and Viruthagiri, 2010; Tanimu et al., 2014). The effect of sugars is best seen in the evolution of the pH. A normal rate for fermentation at 20-40° C. will lead to visible decrease in the pH of the leachate from near neutral to pH 5 in 24-48 hours. The pH will usually reach ≤4.0 in 2-5 days. Once reaching ~pH 4, in normal conditions the acidification trend will continue and the mixture will stabilize at pH approximately 3.4-3.6 after 7-14 days. Crossing the threshold of pH 4 takes significantly longer then the initial pH drop owing to the logarithmic function of the $[H^+]$ and the increasing inhibitory effect of fermentative metabolites leading to negative feedback inhibition to the targeted fermentation itself. Changes in acidity should be evaluated based on the rate of change in proton concentration ($[H^+]$) and not based on the change in pH.

If pH of the fermenting waste does not reach target parameters for food waste stabilization with suitable amendments added, the target pH can be reached by amended with food-grade lactic acid.

The following guidelines are used to determine the amount of initial fermentable carbohydrates (sugars and hydrolysable starch). If the total concentration of fermentable sugars is very low (i.e., 0-10 g/kg), or the ratio between fermentable nitrogen and fermentable carbohydrates is very high, then acidification does not occur and the fermentation leachate turns directly alkaline (Weinberg et al., 2003). Insufficient fermentable sugars (i.e., water soluble carbohydrates) or too little fermentable sugars relative to fermentable nitrogen will lead to initial acidification (acid dip), but eventually, as insufficient metabolic inhibitors of putrefaction (such as $H^+$, alcohols, organic acids, volatile esters and carbon dioxide) accumulate, the pH bounces back toward neutral or alkaline due mostly to ammonia and organic amines produced during protein fermentation. Yet, if sufficient sugars and starch are available or the ratio between fermentable carbohydrates (e.g., sugars and starch) on the one hand and nitrogen on the other hand is high, the fermentation mixtures stabilize at acidic values (pH 3.2-3.8). Some secondary metabolites of sugar fermentation are particularly efficient against alkalization. For example a proportion of lactic acid to acetic acid to crude protein of 92:17:113 g/kg is stable (Weinberg et al., 2003). If this method is applied correctly, the biological waste is stable and acidic at room temperature for long time (more than 12 months) as long as the mixture is kept anaerobic and dehydrated.

Sources of sugar that can be added to the fermentation mixture include but are not limited to: molasses, corn syrup, hydrolysates of starch and cellulose, starch-amylase mixture, commercial sugar, maple syrup, honey, fruit juice, sugar beet juice, and sugar cane juice. Sugar amendments can be added in an aqueous solution. This helps dissolution and dispersion of sugars in the fermentable material and gives fermentative microbes better access to dissolved carbohydrates.

The Brix % (attributable to sugars) of the final leachate of the fermented food waste can be at least 6 Brix %, or at least 8 Brix %, to maintain hyperosmotic stress (a preservative characteristic). Controls for chemical composition can also be done because Brix % is influenced by many chemicals (salts included). The initial leachate from the mixture can be analyzed and the leachate monitored during the first 24 hours of fermentation. Dissolved sugars may be added as needed to the circulated fluid until the Brix % value reaches 9-10 Brix %. After 24 hours or after fermentation has begun however, no more sugars are added unless the Brix % drops below approximately 3-5. A precise value for the recommended concentration of sugars in the final leachate cannot usually be calculated in advance because sugars are not the only inhibitors from the fermentation leachate. Stabilization of the waste is a complex function, and depends (apart from sugars) on many other factors including: pH, and small metabolic inhibitors such as ethanol, lactate, acetate, formate, ethyl acetate, butyrate, propionate, carbon dioxide and others. If the Brix % of the final leachate after 2 weeks of fermentation is too low (approximately ≤3), then insufficient sugars have existed in the initial mixture or the hydrolysis of large carbohydrates was inefficient, or conditions of fermentation have not been followed. If the final Brix % is too high, too much sugar has been added or the amount of starch in the initial mixture was underestimated. The initial sugar concentration should not be as high as to negatively influence the fermentation process owing to osmotic shock. Large sugar concentration in the final mixture (>9) even if the initial sugars was small is good sign and evidence that more sugars have been produced by hydrolysis than used in fermentation. Because salts also produce Brix % readings, corrections have to be made after separate conductivity readings to determine how much of the Brix % readings are owing to sugars. Before doing Brix % readings leachate solutions also have to be filtered because molecules such as starch also give positive Brix % readings. Alternatively, the concentration of sugars can be determined by making direct carbohydrate measurements using conventional chemical methods (Dubois et al., 1956; Liu et al., 1973).

In one embodiment of the method, sugars are not added as an amendment. This generally occurs if the initial concentration of sugars and starch is high enough for fermentation to proceed naturally and target chemistry to be reached without sugar amendment.

In one embodiment of the method starch, flower or low cost starch rich vegetal materials can also be added.

Water amendment is added when fermentation produces too little leachate to circulate through the bioreactor and to allow controlling the fermentation process. Good initial water content for this fermentation is between 60% and 80%. No exact value can be given for the initial water content, because many factors contribute to leachate production and drainage, including permeability, the rate of chemical condensation reactions, and level of cellular disruption. The optimal or suitable abundance of water has to be established from case to case, and will vary with various materials used and is determined by comparisons with leachate produced in earlier fermentations using similar materials.

As a general guideline, one metric ton of fermentation mixture with 70-80% water produces approximately 200 L of leachate in two weeks and the rate of flow through the mixture starts out at around 80-100 L/day and decreases throughout the two-week fermentation process. Only part of the leachate produced can be drained during fermentation. Some residual leachate always remains in the solid fermentate and can be released during post-treatment (FIGS. 1-2). If insufficient leachate is produced then the fermenting materials are too dry, the materials are not fragmented enough for water to be released from the cells, or the mixture does not have sufficient permeability and more lignocellulose fiber has to be added. These situations can be verified by adding known amounts of water or leachate to the bioreactors and monitoring how fast it drains, and by monitoring the leachate produced without water amendment.

The point of consistent leachate production and circulation is so that the fermenting waste is able to maintain homogeneity of microbial byproducts from fermentation, and for the users to be capable to monitor and intervene effectively in the fermentation process. If not enough leachate is being produced (i.e., <200 L/metric ton of food waste at 70-80% initial moisture content) then there are two approaches to solving this issue. First, the fragmentation of the food waste must provide a permeability of liquid equating to a flow rate that is faster than the bioreactor's microbial community can respond. In other words, if the doubling time of bacteria is around 30-40 minutes, the newly amended leachate (with corrected pH, Brix %, etc.) volume needs to be able to permeate the entire bioreactor and the fermenting waste in the bioreactor in shorter time. The second way to fix the issue of leachate production is to outfit the bioreactor with a homogenizer that can mix the fermenting materials evenly whenever newly amended leachate is added back into the bioreactor to correct the fermentation progress. This choice is however more complicated and energy intensive.

Lignocellulosic amendments are materials added as bulking agents (to control granulation, porosity and permeability) or as a means to lower the water content. If the fermentation mixture is too watery (generally above 90%), excess leachate is produced (relative to solid fermentate and fermenter volume) that has to be handled and treated. Using very watery fermentation mixtures also slows down the accumulation of metabolites in leachate and leads to decreased yield of solid fermentate (FIG. 1) relative to a bioreactor capacity. One solution is to use part of the excess liquid to produce the amendment sugar solutions. Starch rich amendments and fragmented lignocellulose materials (see "Low efficiency, safe biological waste" above) can be used as amendments to lower the water content in fermentation mixtures. Alternatively, some of the leachate produced at the beginning of fermentation can be eliminated early without being recirculated in bioreactors.

Mineral amendments include sodium chloride or sea salt (used to increase salinity, to add minerals, to produce osmotic extraction of water and favor lactate fermentation), sulfite (0.6 g sulfite/kg, used to inhibit polyphenoloxidases; Bolenz et al., 1990), limestone (used to add calcium and to buffer acid production in the initial stages).

5.2.4. Microbial Inoculation

Inoculating with microbial organisms is done with mixed cultures of bacteria and yeasts selected for their capacity to grow in anaerobic (0 ppm $O_2$), acidic (pH≥3.2) and mesophilic (T=20 to 45° C.) conditions, to hydrolyze starch and cellulose and starch to small sugars (mono- and disaccharides of hexoses and pentoses), to ferment sugars to alcohols and organic acids, to be as a community heterofermenters rather than homofermenters, to have low yield of soluble alkali (such as ammonia and organic amines) and that are non-pathogenic, may become pathogenic or may produce hazardous levels of toxins (including antibiotics, bacteriocins, fungicides and chemicals that are toxic to eukaryotes such as food-borne toxins).

Optimization of the chemical environment in the bioreactor is designed temporally around enhancing the microbial activity toward the following sequences of events during decreasing of the pH: (1) amylase activity and production of small carbohydrates at circumneutral and below neutral pH (pH 7-4), (2) fermentation of sugars producing alcohols and lowering the pH (pH from 7 to about 3); and producing and activity of cellulases and amylases capable of operating at acidic pH (e.g., pH 4-3.2 or below).

Types of microorganisms that can be used in inocula are, but not limited to, bacteria and fungi from the genera *Acetobacter, Lactobacillus, Saccharomyces, Bacillus* and *Clostridium*. The inoculate should not contain microorganisms that are pathogenic, may become pathogenic, have pathogenic relatives with which they may do lateral gene exchange, or may produce food-borne toxins.

The microorganisms targeted for this fermentation have (individually or as a group) the following metabolic features: chemo-organotrophs, aerotolerant anaerobes or facultative anaerobes, acidophilic or acid tolerant (pH≥3.2), cellulolithic, amylolytic, mesophilic (T=20 to 45° C.), homo or heterofermenters individually but heterofermenters as a community; fermenting pentoses and hexoses with production of alcohols and organic acids, driving fermentation toward acidic conditions, and producing little amount of amines. Some of the cellulases and amylases produced by some (or all) of these microbes will be active at low pHs (from pH 5 to pH as low as 3.2), (Caf, et al., 2014) and produce small fermentable sugars (mono- and disaccharides; hexoses and pentoses). Fermentation products may include carbon dioxide, alcohols (methanol, ethanol, propanol and butanol) and organic acids (acetic, propionic, butyric, valeric, lactic, citric, and others). Anaerobic respiration of sugars with inorganic chemicals such as sulfate, nitrate or metals can be present but it is not absolutely necessary in carrying out the method. The capacity to ferment or respire proteins and nitrogenous bases should generally be kept low. This can be accomplished by the skilled artisan by controlling the composition of the initial mixture, the types of microbes used, and the progression of fermentation.

This method discourages the growth of monocultures, and homofermentation leading to one or very few secondary metabolites, as well as of microorganisms producing inhibition of microbial growth in the stabilized fermentate by means such as bacteriocins (anti-microbial proteins and antibiotics) and fungicides. The production of some small amounts of such chemicals is in most cases unavoidable, but most microbial inhibition in the stabilized fermentate will come from acidification, anaerobiosis, small sugars and wide diversity of secondary metabolites (that albeit not toxic by themselves, and actually easily digestible at low concentration by microorganisms, they inhibit microbial growth at lower concentration in combination). This is because some invertebrate feeds work by means of producing the growth of rich microbial communities on which invertebrates feed, such as biofloc (a protein rich aggregate of organic material and micro-organisms including bacteria, protozoa, algae, and other microorganisms) or microbe-detrital aggregates.

Although fermentation commonly produces chemicals such as alcohols and organic acids that are toxic to most microorganisms and animals, some invertebrates (for example black soldier fly (BSFL) larvae) are highly tolerant to metabolic inhibitors such as alcohols and organic acids (Green and Popa, 2012).

Methods to enrich and isolate species of microorganisms with the physiology characteristics described above have been widely described in the literature and are well known to the skilled microbiologist (Hungate, 1950; Linden et al., 1992; Ali and Mustafa, 2009; Emeka et al., 2012; Romero-Cortez et al., 2012; Okoronkwo, 2014).

Inocula can be obtained from enrichment cultures or can be mixtures of pure cultures with selected physiological properties. The species composition that is optimal or suitable for a variety of feed sources and incubation conditions can vary greatly and no mixture can be formulated that works best in all conditions. If capabilities for enriching, isolating and selecting specific microorganisms are limited or too expensive, the best next option is to inoculate with fermentation leachate produced by a similar type of input material in prior successful fermentations. Prior fermentation leachate that is to be used for inoculation can be stored refrigerated or at room temperature in anaerobic conditions for up to approximately one year.

The density of microorganisms added to the fermentation mixture is $\geq 10^5$-$10^6$ cells per ml. When primary leachate is used as a source of inoculum the amount added can take into account changes in the pH as well. As a general guideline, if, for example, the pH of the inoculum is 3.5, adding 0.1% inoculum relative to the water content of the source material at pH 7 will produce a mixture with a pH of approximately 6.5.

In one embodiment of this method, the inoculating is performed by mixing biological waste with approximately 0.1-1% formerly fermented material of similar composition.

In one embodiment of this method, if the source material contains microorganisms desired for fermentation at densities sufficient to initiate and control fermentation, then no inoculum has to be added. Examples include materials that are rich in fruit pulp, seeds of skins from wine and cider industry and fruit leftover from the production of juice and fruit preserves that are fresh or fermented but not moldy or putrefied.

In another embodiment of the method, a prolonged fermentation, e.g., a 1-week, 2-week or 3-week fermentation is an optional step to make the nutrients more bioavailable.

In another embodiment of the method, if the feed stock of the fermentation is already properly hydrolyzed and contains adequate nutrition for invertebrates, lactic acid can be added directly to the fermentation mixture and brought to target pH range, then immediately dried. This will enable a prolonged, e.g., 3-week, fermentation process to be bypassed. Adding lactic acid will only work for some feed stocks, e.g., ones that are very edible, e.g., tomato skins.

In this method, the "pickling" effect of the biological waste stabilization is achieved by a diverse spread of microbial secondary metabolites stemming from the complex microbial inoculum as well as byproducts of the chemical environment and amendments added to the fermentation in the bioreactor. These compounds and chemical properties as mentioned before include alcohols, volatile organic acids, esters, sugars, carbon dioxide and acidic pH. The compounds will have the ability to be metabolized further by other microbes and produce no toxic effect on the invertebrates fed with them. No single secondary metabolite (whether lactate, acetate, propionate or ethanol) is targeted in this method, owing to the possibility of enriching specialized decay microorganisms, or to produce excess amount of protein based anti-microbial and fungal production such as bacteriocins. The production of bacteriocin-like compounds of fungicide chemicals is in general to be avoided because it interferes later with the establishment of a rich and active microbial community while feeding the invertebrates.

5.2.5. Mixing

Mixing carried out prior to fermentation has the purpose of homogenizing the fermenting materials to obtain a good dispersion of amendments and inoculated microorganisms in the fermentation mixture. Mixing also helps in the evaluation of the state of the mixture and in making last minute corrections of properties of fermentable material prior to introducing it into bioreactors. Mixing also makes the fermentation mixture appropriate to transfer by means such as pumps, tubes, augers, lifts and conveyors.

In one embodiment of the method, one or more of the pre-treating (or pre-processing) steps is skipped if the skilled artisan has determined that the fermentable food waste is in a state similar with the properties of pre-processed fermentable waste with regard to chemical composition, texture, level of mixing, pathogens level, toxins level and abundance of desirable fermentation microorganisms.

5.3. Fermentation

The fermentation process used in this method is cellulolytic hetero-fermentation of complex mixtures rich in sugars (mainly hexoses and pentoses) with acidification and formation of organic acids (mainly lactate, acetate and pyruvate), alcohols (mainly ethanol), carbon dioxide and secondary esters (mainly ethyl-acetate).

5.3.1. Fermentation Parameters

Fermenting of the method is anaerobic, dry, either batch or continuous flow, and the leachate produced may or may not be drained, monitored, amended and recirculated in bioreactors to control the fermentation process.

"Anaerobicity" is maintained by an airtight bioreactor or injecting a gas, or mixture of gasses, with no oxygen (such as carbon dioxide, nitrogen or methane).

"Dry" as used herein refers to allowing leachate drainage from the fermentation in the bioreactor as the biological activity naturally progresses. In this type of dry fermentation, fermenting materials contain water but are not constantly submerged and the pore spaces between the wet particles can fill with gas as the leachate drains.

In one embodiment of the method, the fermentation can be classified as wet, anaerobic, batch fermentation. "Wet" as used herein refers to not allowing drainage of leachates from the fermentation in the bioreactor and adding homogenization to the fermentation in the bioreactor. Wet fermentation can be done when the fermentation evolves without intervention and there is no need for monitoring and amending the content of bioreactors.

"Batch" (as opposed to continuous flow) as used herein, refers to completely clearing the bioreactor after each fermentation cycle.

In one embodiment of the method, the fermentation can be classified as "continuous flow" fermentation. Continuous flow fermentation is used herein to refer to adding new fermentable materials to a bioreactor, while removing fermented materials without totally emptying the bioreactor.

5.3.2. Types of Fermentation Bioreactors

Fermenting can be done in a wide diversity of bioreactor types and sizes provided that they can maintain anaerobic conditions. Bioreactors and methods for constructing them are well known in the art. Bioreactors include but are not limited to: fermentation chambers, growth chambers, incubators, containers, fermenters and silos of all shapes and sizes, rooms and compartments; silage bags and piles of fermenting materials between walls or in windrows in close spaces or covered with air impermeable materials such as foil, silage bags, fiberglass or wood boards. Depending on the amount of leachate produced and the need for fluid circulation and for adding amendments during fermentation, bioreactors may or may not include a drainage and fluid recirculation system.

Bioreactors can be made of stainless steel, fiberglass, plastic, silicate rocks, or coated with ceramic enamel or ceramic tiles. Using bioreactors comprising materials that interact with fermentation products should usually be avoided. Such materials include corrodible metals, materials that are dissolved in water or acids (such as limestone, calcite, or concrete), or materials that absorb acid and release metals (such as basalt), or porous materials that allow water or air to diffuse.

5.3.3. Monitoring and Controlling Fermentation

While undergoing fermentation in a bioreactor, the fermenting material is maintained under anaerobic conditions. No molding should be visible. The pH of the leachate will evolve initially down below pH 4.0, and should not bounce back above pH 5.0.

Temperature can be maintained and monitored and in certain embodiments, can be in the range 20-45° C. Chemicals that signal or inform about the progression of fermentation are alcohols, organic acids, esters, oxygen, carbon dioxide, hydrogen sulfide, methane, ammonium, and amines.

Temperature can be measured using methods well known in the art using digital or analog thermometers. The pH, ammonium, carbon dioxide, oxygen and hydrogen sulfide can be measured with electrodes using methods well known in the art. Carbon dioxide, oxygen, hydrogen sulfide and methane can be monitored by gas chromatography and alcohols, organic acids, esters and organic amines can be monitored by liquid chromatography, both methods being well known in the art.

If molding is seen (usually begins at the surface), then too much oxygen is present or too little carbon dioxide is produced by fermentation. This can be controlled by using better means to maintain anaerobic conditions and by increasing temperature up to approximately 45° C.

In normal fermentation conditions, at 20-45° C. the pH of the leachate will usually reach pH <5 after 24-48 hours. The pH will then drop to ≤4.0 in 3-7 days. The acidification trend will continue and the mixture will stabilize at approximately pH 3.4-3.6 after 7-14 days. In some cases the pH may become as acidic as 3.2. Because pH is a logarithmic parameter, changes in acidity (a measure of the magnitude of microbial activity) near the stabilization point can be evaluated based on replicate measurements and based on the rate of change in proton concentration ([$H^+$]) rather than change in the actual pH value.

A slow evolution of the initial change in pH (acidification) can be caused by the following: temperature in the bioreactor is too low, not enough sugars are present, or the inoculum is either too little or incorrect with regard to species composition. If the pH of the leachate never turns acidic relative to the pH of the input material, turns directly alkaline, or the pH becomes temporarily acidic but eventually bounces back above pH 5 (i.e., alkalization), then insufficient fermentable sugars are present, not enough inhibitors of protein fermentation are produced (such as alcohols, organic acids and esters), and/or the N:C ratio is too high (in most cases owing to too high proportion of animal parts and dairy relative to fermentable carbohydrates). This can be controlled by adding more starch and sugars to manipulate the fermentation leachate to approximately 8-10 Brix % and, if the fermentation is out of control owing to mismanagement, the process can be completely stopped by amending with organic acids (acetic and/or lactic), ethanol and sugars.

If the fermentation material becomes rich in alcohols (especially ethanol), but remains low in acids (especially lactic and acetic), then mostly alcohol fermentation has occurred. This could be the result of the input materials that are too rich in fermentable carbohydrates and/or starch, or inoculum that was too rich in alcohol producing microorganisms (such as yeasts) and too poor in acidogenic microorganism (such as acidogenic bacteria). In this case, the final mixture contains too much ethanol, insufficient carboxylic acids are made (such as lactic, acetic, propionic and butyric) and no inhibitory esters are formed (such as ethyl acetate). This mixture is not stabilized, and has the possibility of decaying upon storage. This situation can be partly corrected by adding acetic and/or lactic acid to the mixture as amendments to the circulating leachate during fermentation, by adding acetogenic microorganisms during fermentation, and/or brief exposure of circulating leachate to air to assist the growth of acetogenic bacteria. However, exposure to air has to be done under well controlled conditions because it may also lead to consumption of the ethanol forming acetate, and can also lead to the growth of aerobic and microaerophilic microorganisms such as food-borne pathogens and molds.

In one embodiment of the method, faster fermentation rates can be obtained (and shorter turnover time in the bioreactor achieved) by increasing the temperature. Yet, each species of microbes will have an optimal and upper limit for growth, and thus temperature will usually not be increased to a level that inhibits fermentation and changes the microbial community. If acidification is too slow then: too much oxygen is present; temperature is either too low or too high; or too much alkali producing materials are present (such as animal parts, animal waste and dairy); or too much pH buffer(s) is present (such as calcium carbonate), or the wall material of the bioreactor reacts with, or absorbs, acids, or too much fat is present slowing the circulation of water and microorganisms.

The dominant chemicals formed during fermentation are carbon dioxide gas, bicarbonate, ethanol, methanol, propanol, butanol, acetate, propionate, butyrate, valerate, lactate, acids of the citric acid cycle, ethyl acetate, ammonium, and mono- and disaccharides. Gasses that should not be produced (within approximately ≥0.1-1 ppm level of change) include methane, hydrogen sulfide, ammonia, nitrous oxide and volatile chemicals associated with putrefaction. Soluble chemicals that should not be present in the leachate at toxic level include hydrogen sulfide, organic amines (including but not limited to methylamine, ethylamine, putrescine, cadaverine and others), food-borne toxins bacteriocins, antibiotics and fungicides.

During fermentation, the abundance of food-borne pathogens will decrease or remain at levels recognized as safe. Detection or increase in the abundance of food-borne pathogens, including but not limited to: *E. coli, Salmonella, Clostridium botulinum, Shigella, Listeria*, and *Clostridium perfringens*, indicate too much animal or dairy product, contaminated input material, departure from the recommended protocol, the presence of unacceptable materials (i.e., health hazards) in the food waste or poorly applied fermentation protocol. Extensive lists of food-borne pathogens are well known in the art (see, e.g., en.wikipedia.org/wiki/Foodborne_illness, last visited Jul. 2, 2015).

In one embodiment of the method, the fermentation leachate is analyzed and recirculated and sugars are added during fermentation. Sugars can be added during fermentation if the Brix % (owing to sugar and after making salinity corrections) is lower than 4% and if the pH does not remain stable in the acid range approximately 3.2-3.8 but evolves toward and then above pH 5.

In one embodiment of the method, if the fermentation cannot be brought under control within two weeks, acetic acid, ethanol and citric acid are added to stabilize the final product. If the fermentation is not be successful, e.g., owing to a poorly implemented protocol, amendments can be made to the input material (e.g., make it richer in sugars, starch and inoculate) or to the fermentation conditions (e.g., better drainage, control during fermentation and lesser contamination with oxygen).

5.3.4. Fermentation Time and End Point Fermentation Parameters

Fermentation is carried out for at least 5 days. A prolonged fermentation, e.g., a 1-week, 2-week or 3-week fermentation is optional, and can be conducted, e.g., to make nutrients more bioavailable.

To confirm the stability of the final fermentation leachate and of the solid fermentate product a "Stability test" is applied. In this test small volumes of sample are kept in anaerobic conditions at 20-45° C. monitored for 5 days (or faster if incubation is applied) while observing changes in pH, ammonia, and/or molding. If the fermentation leachate and solid fermentate remain chemically stable after 5 days, then the fermentation has self-stabilized and can be harvested and used for post-treatment. Owing to the infinite number of combinations of proportions of stabilizing attributes such as pH and secondary microbial metabolites, listing all exact inhibiting cocktails is unfeasible. Stabilization of waste is in this case not judged based on the specific chemical composition but actually on the "stability test" shown above.

In one embodiment of the method, small samples of leachate and fermentate being tested for stability can be warmed to increase microbial activity. This will shorten the amount of time needed to judge stability of final fermentation products.

5.4. Post-treating the Fermentation Product

The fermentation product has a solid fermentate fraction and a fermentation leachate fraction. Some invertebrates such as black soldier fly larvae (BSFL) can eat the fermented materials without further processing. Yet, in most cases the fermentation does not occur in the same place with the growth of the invertebrates and invertebrate feed produced has to be dry and shelf stable (and can be packaged and shipped at low cost).

5.4.1. Separating Solid Fermentate and Fermentation Leachate

Fermentation leachate is separated from solid fermentate in two stages: drainage of leachate during fermentation and dewatering of the solid fermentate. Dewatering serves the purpose to lower the moisture content and decreasing the cost of transport and evaporation, and can be done with a variety of techniques including vacuum filtration, centrifugation, squeeze pressing and others.

5.4.2. Converting Solid Fermentate to Invertebrate Feed

To make stable and dry invertebrate feed, the solid fermentate is ground, dried and milled. A wide variety of art-known methods are available to the skilled artisan and can be used to perform these actions.

5.4.3. Invertebrate Feed Product

The invertebrate feed product ("invertebrate feed," FIG. 2) is a nutrient- and energy-rich material used to feed some invertebrates directly (such as black soldier fly larvae), or it can be pH modified and used to feed invertebrates that are less tolerant of acidic feed (such as annelid worms), or included in feed formulae for growing invertebrates such as shrimp, prawn, crayfish, mollusks and various insects. Feed formulations vary widely among various invertebrates, and the feed for each invertebrate may require specific amendments such as protein, fat, sugars, nitrogenous bases, vitamins, antioxidants and minerals.

5.4.4. Fermentation Leachate

Fermentation leachate (FIG. 2) is a liquid rich in nutrients and energy and can be used for a variety of applications included but no limited to: production of melanin, fertilizers, feed ingredient, seeding material for fermentation and source of organic chemicals such as alcohols, organic acids, esters and sugars.

5.5. Advantages of the Method

Unlike silaging and other lactic acid fermentation methods, which have specific and low diversity input materials and often produce lactic acid as their sole or primary product, the present method is intentionally not limited to the types of input materials and seeks to produce a wide variety of volatile acids, alcohols, and volatile esters. Unlike silaging, air can be allowed to mix with the leachate, in controlled conditions, in order to control anaerobic decay.

Unlike food waste degradation by earth worms, a neutral pH process that is commonly used for food waste disposal, the present method is maintained at a low (acidic) pH, which is incompatible with the earth worm technology. The food wastes that can be used in the method are rich in fermentable carbohydrates (which tend to evolve acidic in early fermentation stages) and decomposition of food waste in neutral and alkaline pH results in odors, methane and health hazards.

Unlike composting (which requires high abundance lignocellulose materials, high C:N ratio, low abundance of easily fermentable materials and degrades in most cases more than 50% of the organic carbon, organic nitrogen and energy from input materials), the present method works with very low lignocellulose materials, can use upwards to 100% fermentable food waste and very little proportion of nutrients and energy from input materials is wasted.

Unlike alcohol fermentation, this process generates a mixture of alcohols, organic acids and esters Unlike lactic fermentation, this process generates a mixture of organic acids and inhibition of ammonifiers is achieved without bacteriocins.

Unlike acetic acid fermentation, this method produces a wide variety of organic acids. The present process is anaerobic and most acetic acid is produced by fermentation of sugars and not by oxidation of ethanol.

Unlike Bokashi fermentation, the present process is controlled and no oxygen is allowed to enter the system. Furthermore, unlike Bokashi fermentation, specific microorganisms are added depending on to the composition of the food waste and desired final composition. Bokashi fermentation, by contrast, is a batch process with no subsequent intervention and is undertaken with exposure to air. Lastly, Bokashi fermentation is not a well-defined or precisely controlled technology, and production of molds is allowed because the final product is further decayed underground and becomes fertilizer rather than animal feed (Yamada et al., 1998). In Bokashi fermentation, the production of mycotoxins (such as aflatoxin) by uncontrolled molds is not a problem.

Unlike Bokashi fermentation, the present method uses a small amount of bran (5-10% relative to dry weight) in contrast to the 40% bran relative to wet weight recommended in Bokashi fermentation (Yamada and Xu, 2001).

Leafy biomass and food waste can be used as starting waste materials to be processed by the method. In an embodiment, the abundance of cellulosic material is low because lignocellulose is very poor in nitrogen, and takes many months to decay. In another embodiment, cellulosic materials (such a paper and woody biomass) can be used as waste to be processed according to the method.

Bokashi fermentation uses a controlled C:N ratio of 10:1. By contrast, the C:N ratio in the present method can be much higher (20:1 and above) because the present method can produce a maximum amount of secondary metabolites quickly using a minimum amount of microbial biomass produced during the fermenting step.

In addition, the chemical evolution of the fermentation process is monitored and fermentation is stopped (stopped by human intervention i.e., leachate drained, fermented food waste dried and milled) when the product has matured and the liquid has reached specific target parameters.

Unlike other methods known in the art for reclaiming nutrients from biological waste (such as fermentation and composting), the present method works robustly with post-consumer food waste rich in salts and other preservatives and chemical amendments. For example, black soldier fly larvae are very tolerant to chemical stress and can be fed with invertebrate feed produced by the present method from post-consumer food waste.

Unlike other methods to extract value from cellulosic biomass (such as cellulosic ethanol industry where efficiency is hampered by chemical diversity and variable mixtures of hexoses and pentoses) this method is robust to the ratio between hexoses and pentoses and all carbon is eventually utilized either as feed or to produce metabolic inhibitors of decay.

At the end of the process, virtually all of the nutritional and energetic value of the food waste can be reclaimed, something that cannot be achieved by any other method presently available.

Unlike prior art methods such as anaerobic digestion and composting, the present method requires only a short (2 weeks) fermentation time, and the product is stabilized from protein fermentation and alkalinization by generating a fermentation leachate with high concentrations of organic acids, alcohols, esters and sugars. Unlike prior art methods such as pickling fruits and vegetables, no salts, citrate, acetate or other chemical preservatives are added.

The fermentation carried out in the present method preserves, rather than mineralizes, organic nutrients and maintains chemical energy in the system.

One benefit of the present method is lower cost to conduct the method, which can be achieved by eliminating water by squeeze-pressing, partial hydrolysis of cellulose and starch, partial decomposition of the vegetal cell walls (while maintaining the integrity of the cell membranes), low level of decomposition of proteins, fats and nucleic acids, and high concentration of metabolic inhibitors and pest deterrents such as acidity, alcohols, soluble and volatile organic acids, esters and small sugars.

Unlike prior art fermentation methods (e.g., anaerobic digestion and composting), the present method produces little carbon dioxide, little ammonia and no methane.

The present method is different from anaerobic digestion and composting, both of which are commonly used to mineralize food waste. Rather, mineralization is achieved by the combination of first producing a desired invertebrate feed or invertebrate feed (the process described in this patent application), and then feeding the invertebrate feed to a desired invertebrate. Benefits of the present method (by comparison to anaerobic digestion and composting) include 1) food waste is completely disposed of, and 2) nutrients and energy are reclaimed in the form of invertebrate feed and later protein-rich invertebrate biomass.

This present method can also be utilized linearly with anaerobic digestion to add value to the process. Leachate can be extracted prior to anaerobic digestion to produce melanin. Another benefit of this fermentation in-line with anaerobic digestion is the increase in hydrolysis levels of the input biological matter, and the high concentrations of secondary metabolites created. This provides more bioavailable nutrients for acetogenic bacteria, the precursor bacterial populations to methanogens.

6. EXAMPLE

6.1. Example 1: Production of Invertebrate Meal for Use in Feeding Insect Larvae This example describes the production of invertebrate meal and its use to feed insect larvae.

A bioreactor having a total volume of 200 liters was used. The starting biological waste that was processed in the bioreactor was 150 kg of kitchen food waste and shelf-expired cucumbers. Amendments were spread homogeneously throughout the mixture to ensure the proper evolution of the fermentation. The amendments were 9.38 kg wheat bran, 30 liters of a 20% solution of molasses, and 6.25 liters of biological inoculate obtained from previous fermentation leachates. Previous batches of fermentation leachate were stored and kept chilled to keep as an inoculation for subsequent fermentations. Multiple iterations of this process, for example, 10 or more, resulted in an inoculum very efficient in initiating fermentation towards the desired parameters.

The bioreactor was closed airtight. Twice a week, leachate from the fermentation was drained and poured over the top of the fermenting material. After 4 weeks the pH of the leachate had stabilized to pH 3.4 and the fermentation was stopped. The leachate was drained and removed from the bioreactor.

The solid fermentate, containing approximately 70% water, was ground to a paste and dried in a ventilated greenhouse with mid-day and afternoon temperatures reaching 50-60° C. The final dry material was milled and sieved to a fine powder (<0.5 mm particle size) and used as invertebrate meal for feeding insect (fly) larvae.

The leachate had the following properties: pH 3.4; 8 Brix %; 0.1% ethanol; 1.65% propionic acid and 1.98% acetic acid (organic acid and alcohols were determined by gas chromatography).

The invertebrate meal contained: 8.02% water (based on evaporation at 101° C. to constant weight); 12.68% crude protein (based on Nitrogen×6.25); 11% fat (base on acid hydrolysis/ether extraction); 5.24% ash; 63.06% carbohydrates (by difference); and 402 calories/100 grams.

The invertebrate meal was fed to one-week old Black Soldier Fly larvae, and the growth of the larvae was stopped and the larvae were harvested when the first dark-colored larvae were observed. The results of 55 independent feeding experiments showed a 0.83 average for the food conversion ratio with +/−0.20 standard deviation. It was also verified that crickets will eat the invertebrate meal prepared by this method.

A sample of the methods that are described herein are set forth in the following numbered paragraphs:

1. A method for converting biological waste to invertebrate feed, the method comprising:
   pre-treating biological waste, wherein the pretreating comprises:
      fragmenting the waste,
      reducing microbial contaminants in the waste,
      inoculating the waste with microorganisms, and
      mixing the waste;
   providing a bioreactor;
   performing fermentation of the waste under anaerobic conditions, wherein the fermentation comprises fermenting the waste in the bioreactor to produce a fermentation product comprising fermentation leachate and solid fermentate;
   post-treating the fermentation product, wherein the post-treating comprises:
      separating solid fermentate from fermentation leachate in the fermentation product,
      grinding the solid fermentate,
      dewatering the solid fermentate, and/or
      milling the solid fermentate, thereby producing an invertebrate feed.

2. The method of paragraph 1 wherein the biological waste is optimal biological waste or low efficiency biological waste.

3. The method of paragraph 1 wherein the pre-treating comprises amending the waste with fermentation-optimizing agents.

4. The method of paragraph 1 comprising monitoring the fragmenting continuously and/or controlling the fragmenting to optimize the average particle size and particle size variance.

5. The method of paragraph 1 comprising monitoring the fermenting.

6. The method of paragraph 1 comprising analyzing the fermentation leachate.

7. The method of paragraph 1 comprising controlling the temperature of fermentation.

8. The method of paragraph 1 comprising controlling the pH of fermentation.

9. The method of paragraph 8 comprising adding lactic acid to the fermentation.

10. The method of paragraph 1 comprising controlling the Brix % of fermentation.

11. The method of paragraph 1 wherein the density of microorganisms inoculating the waste is $\geq 10^5$-$10^6$ cells per ml.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

REFERENCES

1. Ali A. A. and M. M. Mustafa, 2009, Isolation, characterization and identification of lactic acid bacteria from fermented sorghum dough used in Sudanese Kisra preparation, Pakistan Journal of Nutrition, 8(11):1814-1818.
2. Bolenz S., H. Omran and K. Gierschner, 1990, Treatments of water hyacinth tissue to obtain useful products, Biological Wastes 33:263-274.
3. Caf, Y., E. Valipour, and B. Arikn, 2014, Study on cold-active and acidophilic cellulase (CMC-ase) from a novel psychotropic isolate *Bacillus* sp. K-11, Int. J. Cur. Biol. Appl. Sci., 3(5):16-25.
4. Cai T., 1993, Stabilization of poultry by-products and waste, and poultry carcasses through direct chemical acidification and lactic acid fermentation. Thesis Cornell University, Ann Arbor. Pp.205.
5. DuBois M., K. A. Giles, J. K. Hamilton, P. A. Rebers and F. Smith, 1956, Colorimetric method for determination of sugars and related substances, Anal. Chem 28:350-356.
6. Emeka N., J. C. Ogbonna, M. C. Ominyi, K. E. Nwagu and G. Gibson-Umeh, 2012, Isolation of citric acid-producing fungi and optimization of citric acid production by selected isolates, Global Journal of Bio-Science and Technology, 1(2):261-270.
7. Green T. R. and R. Popa, 2012, Using black soldier fly larvae (*Hermetia illucens*) for processing organic leachates, J. Econ. Entomol. 105:374-378. doi: http://dx.doi.org/10.1603/EC11192.
8. Hungate R. E., 1950, The anaerobic mesophilic cellulolythic bacteria, Bacteriol. Rev., 14(1):1-49.
9. Kim, H. J., S. H. Kim, Y. G. Choi, G. D. Kim and T. H. Chung, 2006, Effect of enzymatic pretreatmenton acid fermentation of food waste, J. Chem. Technol. Biotechnol., 81:974-980.
10. Linden T., J. Peetre and B. Hahn-Hagerdal, 1992, Isolation and characterization of acetic acid-tolerant galactose-fermenting strains of *Saccharomyces cerevisiae* from a spent sulfite liquor fermentation plant, Applied and Environmental Microbiology, 58(5):1661-1669.
11. Liu D., P. T. S. Wong and B. J. Dutka, 1973, Determination of carbohydrate in lake sediment by a modified phenol sulfuric acid method, Water Research, 7:741-746.
12. Manikandan K. and T Viruthagiri, 2010, Optimization of C/N ratio of the medium and fermentation conditions of ethanol production from tapioca starch using co-culture of Aspergillus niger and Sachormyces cerevisiae, International Journal of ChemTech Research, 2: 947-955.

13. Middleton, T. and P. Ferket, 2001, Effect of level of acidification by phosphoric acid, storage temperature, and length of storage on the chemical and biological stability of ground poultry mortality carcasses. Poult. Sci. 1144-1153.
14. Okoronkwo C. U., 2014, Isolation and characterization of lactic acid bacteria involved in the fermentation of millet and sorgum sold in Nkwo-Achara Market, Abia State, IOSR Journal of Environmental Science, Toxicology and Food Technology, 8(9):42-45.
15. Romero-Cortez T., V. Robles-Olvera, G. Rodriguez-Jimenes and M. Ramírez-Lepe, 2012, Isolation and characterization of acetic acid bacteria in cocoa fermentation, African Journal of Microbiology Research, 6(2):339-347.
16. Tanimu M. I. T. I. Mohd Ghazi, R. M. Harun and A. Idris, 2014, Effect of carbon to nitrogen ratio of food waste on biogas methane production in a batch mesophilic anaerobic digester, International Journal of Innovation, Management and Technology, 5:116-119.
17. Tembhurkar A. R. and V. A. Mhaisalkar, 2007, Studies on hydrolysis and acidogenesis of kitchen waste in two phase anaerobic digestion. Journal of the IPHE, India, 2007-2008(2):10-18.
18. Yamada K., H. L. Xu, S. Kato, M. Fujita, K. Katase and H. Umemura, 1998, Properties and applications of an organic fertiliser with microbial inoculant added, Nature Farming and Sustainable Environment, 1:13-25.
19. Yamada K. and H. L. Xu, 2001, Properties and applications of an organic fertilizer inoculated with effective microorganisms, Journal of Crop Production, 3(1):255-268.
20. Weinberg, Z., G. Ashbell and Y. Chen, 2003, Stabilization of returned dairy products by ensiling with straw and molasses for animal feeding. Journal of Dairy Science, 86(4):1325-1329.

What is claimed is:

1. A method for converting a biological waste to a feed for black solider fly larvae, the method comprising:
   pre-treating the biological waste, wherein the pretreating comprises:
      fragmenting the waste,
      reducing microbial contaminants in the waste,
      inoculating the waste with microorganisms, and
      mixing the waste;
   providing a bioreactor;
   performing fermentation of the waste under anaerobic conditions, wherein the fermentation comprises fermenting the waste in the bioreactor to produce a fermentation product comprising fermentation leachate and solid fermentate;
   post-treating the fermentation product, wherein the post-treating comprises:
      separating solid fermentate from fermentation leachate in the fermentation product,
      grinding the solid fermentate,
      dewatering the solid fermentate, and/or
      milling the solid fermentate,
   thereby producing the feed for black solider fly larvae.

2. The method of claim 1 wherein the biological waste is optimal biological waste or low efficiency biological waste.

3. The method of claim 1 wherein the pre-treating comprises amending the waste with one or more fermentation-optimizing agents selected from the group consisting of bran, sugars, water, lignocellulose, sodium chloride, sulfite and limestone.

4. The method of claim 1 comprising fragmenting the waste to a particle size of approximately 1 mm to 50 mm.

5. The method of claim 1 wherein the fermentation of the waste occurs at a temperature of approximately 20-45° C.

6. The method of claim 1 wherein the pH of the fermentation leachate is less than or equal to 5.0 after 24-48 hours.

7. The method of claim 1 wherein the Brix % of the feed is at least approximately 6%.

8. The method of claim 1 wherein the density of microorganisms inoculating the waste is $\geq 10^5$-$10^6$ cells per ml.

9. The method of claim 1 wherein the pre-treating comprises amending the waste with fermentation optimizing agents consisting essentially of bran, a molasses or corn syrup solution and a biological inoculate.

10. The method of claim 1 wherein reducing microbial contaminants in the waste comprises inoculating the waste with a consortium of microorganisms selected from the group consisting of bacteria and fungi from the genus *Acetobacter, Saccharomyces, Lactobacillus* and *Clostridium*.

11. The method of claim 1 wherein the pH of the fermentation leachate is less than or equal to approximately 4.0 in 3 to 7 days.

12. The method of claim 1 wherein the Brix % of the feed is at least approximately 8%.

13. The method of claim 1 wherein after the fermentation leachate is separated from the solid fermentate, the leachate has a pH of approximately 3.4 and a Brix % of approximately 8%.

14. The method of claim 1 wherein the feed contains approximately 8% water, 12-13% crude protein, 11% fat, 5% ash and 63% carbohydrates.

15. A method for converting a biological waste to shelf-stable invertebrate feed, the method comprising:
   pre-treating the biological waste, wherein the pretreating comprises:
      fragmenting the waste,
      reducing microbial contaminants in the waste,
      inoculating the waste with microorganisms, and
      mixing the waste;
   providing a bioreactor;
   performing fermentation of the waste under anaerobic conditions, wherein the fermentation comprises fermenting the waste in the bioreactor to produce a fermentation product comprising fermentation leachate and solid fermentate,
      wherein the pH of the fermentation leachate is less than or equal to approximately 4 in 3 to 7 days;
   post-treating the fermentation product, wherein the post-treating comprises:
      separating solid fermentate from fermentation leachate in the fermentation product,
      grinding the solid fermentate,
      dewatering the solid fermentate, and/or
      milling the solid fermentate,
   thereby producing the invertebrate feed wherein the invertebrate feed has a stable pH of approximately 3.4.

16. The method of claim 15 wherein the fermentation does not produce, within approximately $\geq 0.1$-1 ppm level of change, methane, hydrogen sulfide, ammonia, nitrous oxide and volatile chemicals associated with putrefaction.

17. The method of claim 15 wherein the invertebrate feed is stable and acidic at room temperature for at least 12 months when kept anaerobic.

18. A method for converting a biological waste to an invertebrate feed, the method comprising:
(a) pre-treating the biological waste, wherein the pretreating comprises:
fragmenting the waste,
reducing microbial contaminants in the waste,
inoculating the waste with non-pathogenic mesophilic microorganisms at a density of $10^5$-$10^6$ cells per ml, wherein the microorganisms are:
chemo-organotrophs,
aerotolerant anaerobes or facultative anaerobes,
acidophilic or acid tolerant at pH >3.2,
cellulolithic,
amylolytic, [or]
homofermenters or heterofermenters individually and heterofermenters as a community;
wherein the microorganisms have the capacity to:
ferment pentoses and hexoses, thereby producing alcohols and organic acids,
drive fermentation toward acidic conditions,
produce low levels of soluble alkali,
hydrolyze cellulose and starch to monosaccharides or disaccharides of hexoses or pentoses, and
wherein the microorganisms comprise microorganisms from the genera *Acetobacter, Lactobacillus, Saccharomyces*, and *Clostridium*, and
mixing the waste;
(b) providing a bioreactor;
(c) performing fermentation of the waste under anaerobic conditions in the bioreactor, thereby producing a fermentation product comprising fermentation leachate having a Brix % of 6-10 and solid fermentate, wherein performing fermentation comprises circulating fermentation leachate in the bioreactor during fermentation,
(d) monitoring the fermentation, wherein monitoring comprises analyzing the fermentation leachate,
wherein analyzing the fermentation leachate comprises determining pH, fermentable sugar content and nitrogen content of the fermentation leachate,
(e) controlling progression of the fermentation, wherein controlling progression of the fermentation comprises maintaining:
temperature at 20-45° C.,
pH <5,
Brix % at 9-10 Brix % during the first 24 hours of the fermentation, and
Brix % at least 3 Brix % after 24 hours of the fermentation,
(f) post-treating the fermentation product, wherein the post-treating comprises:
separating solid fermentate from fermentation leachate in the fermentation product,
grinding the solid fermentate,
dewatering the solid fermentate, and/or
milling the solid fermentate,
thereby producing the invertebrate feed.

19. The method of claim 18 wherein the biological waste is optimal biological waste or low efficiency biological waste.

20. The method of claim 18 wherein the pre-treating comprises amending the waste with one or more fermentation-optimizing agents selected from the group consisting of bran, sugars, water, lignocellulose, sodium chloride, sulfite and limestone.

21. The method of claim 18 comprising fragmenting the waste to a particle size of approximately 1 mm to 50 mm.

* * * * *